United States Patent
Bonner

(10) Patent No.: US 9,047,755 B2
(45) Date of Patent: Jun. 2, 2015

(54) HYGIENE COMPLIANCE SYSTEM AND METHOD

(75) Inventor: James Bonner, Londonderry (GB)

(73) Assignee: Itronik Interconnect Limited, Loughrea (IE)

( * ) Notice: Subject to any disclaimer, the term of this patent is extended or adjusted under 35 U.S.C. 154(b) by 0 days.

(21) Appl. No.: 13/515,923

(22) PCT Filed: Dec. 14, 2010

(86) PCT No.: PCT/EP2010/007607
§ 371 (c)(1),
(2), (4) Date: Sep. 21, 2012

(87) PCT Pub. No.: WO2011/072837
PCT Pub. Date: Jun. 23, 2011

(65) Prior Publication Data
US 2013/0027199 A1 Jan. 31, 2013

(30) Foreign Application Priority Data
Dec. 14, 2009 (IE) .................................. S2009/0935

(51) Int. Cl.
G08B 1/08 (2006.01)
G08B 23/00 (2006.01)
G06F 17/00 (2006.01)
B67D 1/00 (2006.01)
G08B 21/24 (2006.01)
G06F 19/00 (2011.01)
(Continued)

(52) U.S. Cl.
CPC .............. *G08B 21/24* (2013.01); *G08B 21/245* (2013.01); *G06F 19/327* (2013.01); *G08B 21/02* (2013.01); *A47K 5/1217* (2013.01)

(58) Field of Classification Search
CPC ...... G08B 21/245; G08B 21/24; G08B 21/02; G08B 21/287; A61L 2/18; G06F 19/327; G06F 19/3418; G06F 19/3493; A47K 2005/1218; A47K 5/1217; A61B 5/1113
USPC ........ 340/539.11, 573.1, 572.1, 539.1, 573.4, 340/539.13, 539.23, 691.3, 567, 529, 573.5, 340/539.12, 542, 540; 705/2, 8; 137/552.7, 137/552.9; 4/623; 222/39; 700/231
See application file for complete search history.

(56) References Cited

U.S. PATENT DOCUMENTS 6,236,317 B1 * 5/2001 Cohen et al. ............... 340/573.1
6,426,701 B1 * 7/2002 Levy et al. .................. 340/573.1
(Continued)

OTHER PUBLICATIONS

International Search Report and Written Opinion for PCT/EP2010/007607, mailed Mar. 18, 2011.

*Primary Examiner* — Mirza Alam
(74) *Attorney, Agent, or Firm* — Withrow & Terranova, P.L.L.C.

(57) ABSTRACT

A hygiene compliance system comprising personnel tags each having a respective status indicator that may be set to a first value indicating hygiene compliance or to a second value indicating hygiene non-compliance. Monitors for target zones, e.g. patients' beds, detect the presence of the personnel tags at the target zone. Monitors for hygiene stations, e.g. washbasins, detect the presence of the tags at the hygiene stations. When the hygiene station monitor detects that a hygiene station has been used, the respective tag is set to the first value. The target zone monitor checks the status of tags detected in its target zone and may issue a warning if the status indicates hygiene non-compliance. When the person leaves the target zone, the target zone monitor changes the respective tag's status to the second value.

28 Claims, 2 Drawing Sheets

(51) Int. Cl.
*G08B 21/02* (2006.01)
*A47K 5/12* (2006.01)

(56) References Cited

U.S. PATENT DOCUMENTS 7,812,730 B2 * 10/2010 Wildman et al. .......... 340/573.1
2008/0001763 A1 * 1/2008 Raja et al. .................. 340/573.1
2008/0167573 A1 * 7/2008 Stivoric et al. ................ 600/549
2008/0246599 A1 * 10/2008 Hufton et al. ................. 340/529
2009/0051545 A1 * 2/2009 Koblasz ..................... 340/573.1
2009/0091458 A1 * 4/2009 Deutsch ..................... 340/573.1
2011/0121974 A1 * 5/2011 Tenarvitz et al. ........... 340/573.1
2012/0212582 A1 * 8/2012 Deutsch ........................... 348/46

* cited by examiner

HYGIENE COMPLIANCE SYSTEM AND METHOD

This application is a 35 USC 371 national phase application of International application PCT/EP2010/007607 filed Dec. 14, 2010, which claims priority to Irish national application S2009/0935 filed Dec. 14, 2009, the disclosures of which are incorporated herein by reference in their entireties.

FIELD OF THE INVENTION

The present invention relates to monitoring hygiene activity.

BACKGROUND TO THE INVENTION

Hygiene activity, for example hand washing, is typically monitored by means of visual observation and manual logging of the event. To a large extent, therefore, whether or not the required hygiene standards are met depends on the diligence of the individuals involved.

It would be desirable to provide a hygiene monitoring system that is less reliant on human diligence.

SUMMARY OF THE INVENTION

A first aspect of the invention provides a hygiene compliance system comprising
  at least one personnel tag for carrying by a respective person, said at least one personnel tag being associated with a respective status indicator that is settable to a first value indicating hygiene compliance or to a second value indicating hygiene non-compliance,
  at least one target zone monitoring apparatus for monitoring a respective target zone, said at least one target zone monitoring apparatus including means for detecting the presence of said at least one personnel tag at the respective target zone,
  at least one hygiene station monitoring apparatus for monitoring a respective hygiene station,
  wherein, upon determining that the respective hygiene station has been used, said at least one hygiene station monitoring apparatus is configured to cause the respective status indicator of the relevant personnel tag to be set to said first value,
  and wherein, upon determining the presence of any one of said at least one personnel tag at said respective target zone, said target zone monitoring apparatus is configured to determine the value of the respective status indicator.

A second aspect of the invention provides a method of monitoring hygiene compliance in a system comprising
  at least one personnel tag for carrying by a respective person, said at least one personnel tag being associated with a respective status indicator that is settable to a first value indicating hygiene compliance or to a second value indicating hygiene non-compliance,
  at least one target zone monitoring apparatus for monitoring a respective target zone, said at least one target zone monitoring apparatus including means for detecting the presence of said at least one personnel tag at the respective target zone,
  at least one hygiene station monitoring apparatus for monitoring a respective hygiene station,
  said method comprising, upon determining that a hygiene station has been used, causing the respective status indicator of the respective personnel tag to be set to said first value, and
  upon determining the presence of any one of said at least one personnel tag at said respective target zone, determining the value of the respective status indicator.

Preferred embodiments of the invention provide a system whereby the monitoring is performed by means of a combination of four core technologies and their adoption. Component parts of the system can be adapted through the change of software/firmware for different applications. For example a hand hygiene monitoring module may be adapted to monitor activity at antibacterial dispensers and water wash stations.

In the preferred embodiment, a hygiene station monitoring apparatus for use in the system is arranged to support an ID communications channel, and comprises means for detecting presence of a person, means for counting the duration that a person remains in the hygiene station, e.g. a wash zone, preferably to a one second resolution, preferably means for storing records in a memory, preferably a volatile memory, and preferably means for communicating and downloading monitoring data to a server and/or a personnel tag.

The preferred system provides for evaluating hygiene compliance in a facility and typically comprises a plurality of target zones (i.e. locations in which individuals are required to maintain hygiene standards, e.g. a patient's bed); a plurality of hygiene stations (e.g. sinks and/or dispensers of cleaning substances); personnel tags for personnel using the system; and detectors, e.g. readers, at the stations (preferably at both the target zones and the hygiene stations) capable of detecting the presence of said personnel tags. The system may also include control means for detecting whether a personnel tag accessed at a station. Preferably, each station has a unique station identifier and each personnel tag has a unique personnel identifier, making possible the tracking of specific worker interactions. Individual stations can also bear unique identifiers.

The personnel tags conveniently comprise a machine readable sensor such as an RFID tag. The hand hygiene status of a user bearing the personnel tag is preferably stored on the personnel tag itself but can also, or alternatively, be stored on a server, e.g. central processor, linked to multiple target zones and one or more hygiene stations. The central processor may generate reports of compliance rates and hygiene activity. Such reports might be averaged for the facility or specific to individual workers. They can include the number of interactions, the number of interactions where proper hygiene was practiced, the number of interactions where proper hygiene was not practiced and/or whether proper hygiene was practiced after an interaction, e.g. at a target zone.

Preferably, the target zones include an alarm device which can provide a warning if a personnel tag having a status other than required approaches the station. The warning can be audible and/or visual. Preferably, means are provided for defining a perimeter about the station within which the personnel tag is considered present at the station. for the preferred system is capable of personnel detection, and monitoring, collecting and storing the hygiene activity. The system typically comprises a personnel detector, a monitoring and data collecting module, and means for communicating data to the server or other system component.

In preferred embodiments, a respective individual identification device, preferably includes means for recording hygiene activity events. The device includes means for storing ID information and means for communicating with other components of the system, especially said person detection device.

Advantageously, said personnel tags include a status indicator to indicate a hygiene status, e.g. a hand hygiene status, of the person bearing the tag. The status indicator may provide an audible and/or visual indication of a change in status.

Preferred systems may support other functions such a temperature monitoring, laundry temperature and cycle counts for smart uniforms.

Advantageously, the system may be used to ensure that a person performs a hand hygiene event prior to patient contact.

A third aspect of the invention provides a hygiene compliance system comprising at least one tag incorporated into a respective washable item, especially an item of clothing, said at least one tag being associated with a respective status indicator that is settable to a first value indicating hygiene compliance or to a second value indicating hygiene non-compliance, said at least one tag further including a temperature sensor that, in response to detecting a temperature above a threshold temperature, is configured to cause said status indicator to be set to said first value.

Preferably, said at least one tag includes an alarm device, preferably an audio alarm device, said at least one tag including means for activating said audio alarm device in response to determining that the respective status indicator is set to said second value.

Optionally, said at least one tag comprises means for maintaining its respective status indicator. Alternatively, said respective status indicator is maintained by a central processor.

Preferably, said at least one tag comprises a counter with which said at least one tag is configured to count the number of times said respective status indicator is set to said first value.

Preferably, said system, e.g. via at least one tag, or via said central processor, is configured to set said respective status indicator to said second value after a period of time has elapsed after having been set to said first value. Optionally, said respective status indicator is set to said second value depending on the date and/or time. To these ends, each tag may include a timer and/or a clock, especially a clock that supports a calendar.

The embedded tags are particularly suitable for use with machine washable articles such as clothing, bed linen, and towels. By way of example, the temperature threshold may be approximately 70° C.

A fourth aspect of the invention provides a method of monitoring hygiene compliance for an item, especially of washable items such as clothing, said item comprising a tag associated with a respective status indicator that is settable to a first value indicating hygiene compliance or to a second value indicating hygiene non-compliance, said tag further including a temperature sensor, said method comprising setting, in response to said temperature sensor detecting a temperature above a threshold temperature, said status indicator to said first value.

Preferred features of the invention are recited in the dependent claims.

Further advantageous aspects of the invention will be apparent to those ordinarily skilled in the art upon review of the following description of a preferred embodiment and with reference to the accompanying drawings.

BRIEF DESCRIPTION OF THE DRAWINGS

An embodiment of the invention is now described by way of example and with reference to the accompanying drawings in which.

DETAILED DESCRIPTION OF THE DRAWINGS

Figure 1A:
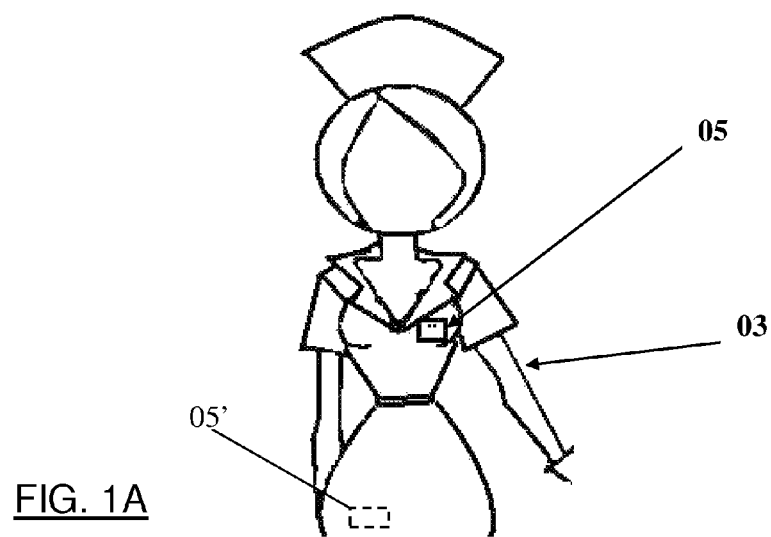
FIGS. 1A to 1C show schematically respective parts of a hygiene compliance system embodying one aspect of the present invention.
Figure 1B:
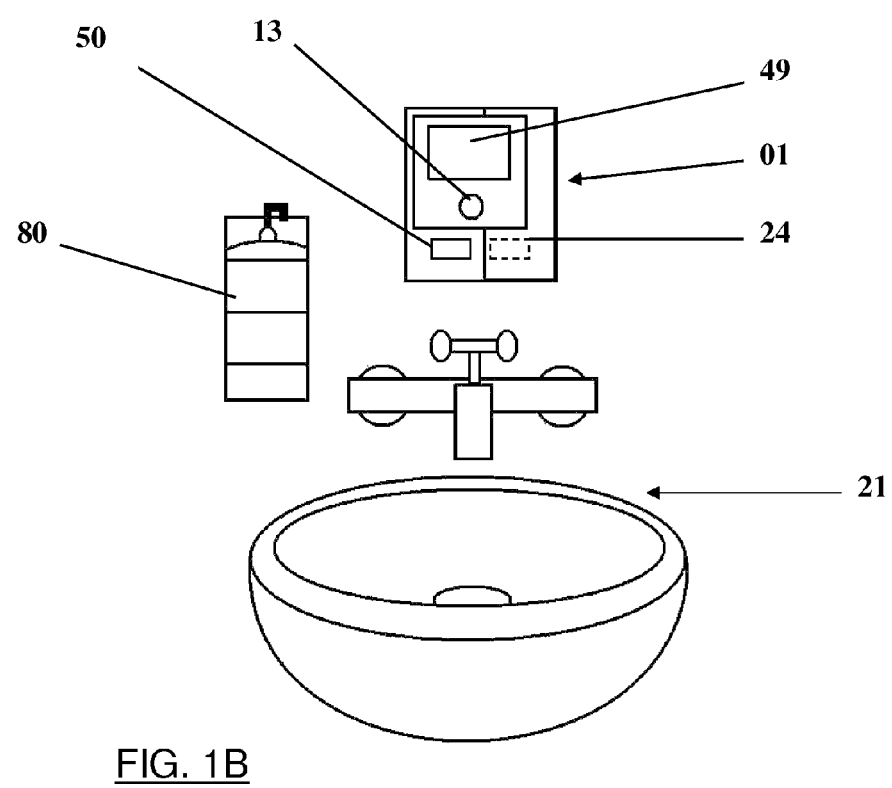
Figure 1C:
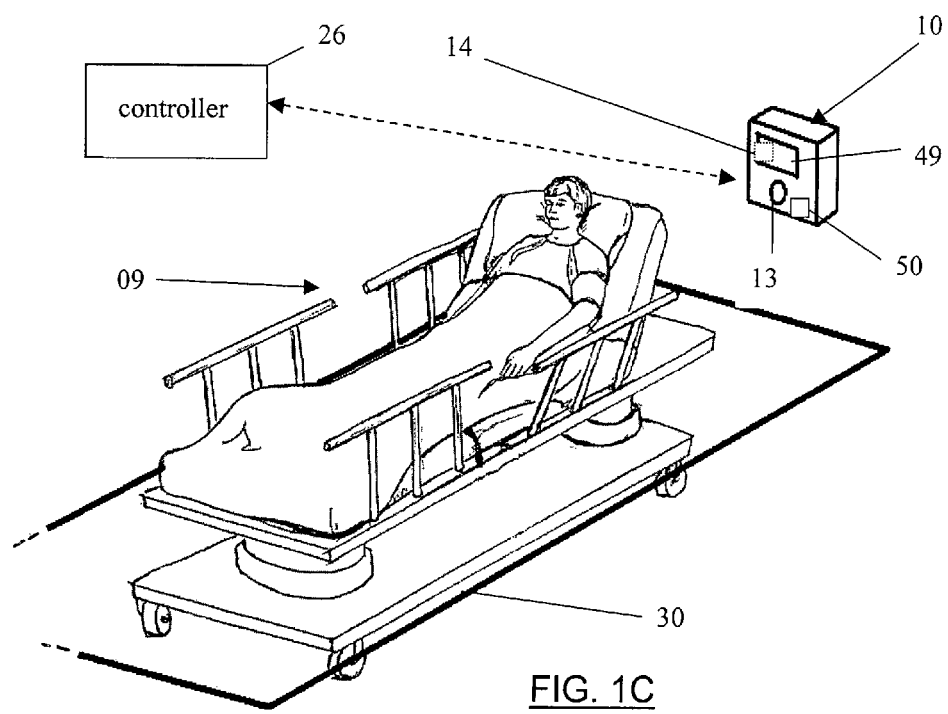

FIGS. 1A to 1C together show components of a preferred hygiene compliance system embodying the invention. By way of example the system of FIGS. 1A to 1C is described in use as a hand hygiene compliance system in, for example, a healthcare facility. FIG. 1A shows a person 03, such as a doctor, nurse or visitor, being one of typically a plurality of users of the system who are expected to maintain a standard of hygiene which, in this example, involves cleaning their hands, e.g. in a sink or using a dispenser of disinfectant or other cleaning product. Each user is provided with a personnel tag 05, which preferably incorporates, or is otherwise associated with, a unique identifying number, but may not for privacy reasons. The tag 05 preferably includes some form of proximity locator and/or local communication means, e.g. a wireless transceiver. For instance, in a preferred embodiment of the invention, the tag 05 incorporates a Radio Frequency Identification (RFID) tag/device or other transponder. The preferred tag 05 includes a wireless communication device (not shown) enabling the tag 05 to communicate with other devices in the system, as is described in more detail hereinafter. The preferred tag 05 includes a locating device (not shown) that allows the tag 05 to be detected, and preferably identified, by other devices in the system. To these ends, the tag 05 conveniently includes the aforesaid RFID device, but may additionally include a wireless transceiver. The tag 05 may be worn like a badge or otherwise carried by the user, typically in, on or incorporated into their clothing.

Figure 2:
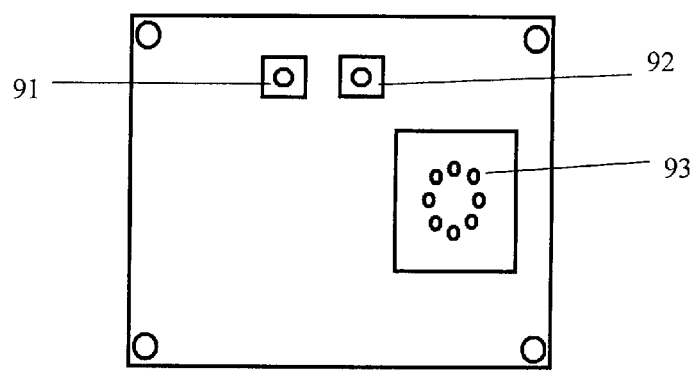
FIG. 2 is a schematic view of a personnel tag suitable for use with the system of FIGS. 1A to 1C.

The system is intended to promote hygiene standards compliance in at least one but typically a plurality of target zones which, in the present example, are patient contact locations such as a hospital bed 09 (FIG. 2). The, or each, target zone is provided with a monitoring apparatus 10, which in the present example may be referred to as a patient location module 10. The monitoring apparatus 10 comprises and/or is in communication with one or more sensors for detecting the approach of persons 03 and/or the approach of the tag 05. Multiple sensors and/or sensors of different types could be provided for these purposes. For instance, a passive infrared radiation (IR) sensor 13, or other proximity detector capable of detecting the approach of a person may be provided along with an RFID transceiver 14 for reading the RFID tag 05 in the personnel tag 05. This would allow the RFID transceiver 14 to remain off until the bed 09 is approached, i.e. until the PIR detector 13 detects the approach of a person, saving energy and reducing electromagnetic noise in the environment. Alternatively, the proximity detector may be omitted and the monitoring apparatus 10 and tag 05 may communicate using respective RFID devices, e.g. the RFID transceiver at the monitor 10 may be configured to detect and communicate with the RFID transponder in the tag 05, or the RFID transponder in the tag may be configured to detect and initiate communication with the RFID device in the monitor 10. The respective RFID devices may be active or passive as required. It will be understood that alternative means for allowing the monitor to detect the tag 05 and/or person, and to communicate with the tag 05 may be provided using any suitable conventional technology(ies).

In preferred embodiments, the monitoring apparatus 10, by means of one or more sensor, is configured to define a detection perimeter 30 around the target zone, e.g. patient station, with which it is associated. In a simple form the perimeter is defined by the location of the RFID transceiver 14 on the station, the RFID transceiver having a range equivalent to the desired perimeter. The perimeter is preferably about one or two feet from the patient station. If it is too far it might falsely register a contact and if it is too small it might fail to register a contact. Other means for defining a perimeter such as one or more light beam detectors, e.g. PIR detector(s) or through-beam detector(s) may be provided instead or in addition. Such devices may be configured to create light beam(s) defining said perimeter which, if broken by a person approaching a patient station, allow the monitor 10 to detect the presence of the person. Sensors used by the monitoring apparatus 10 may be located separately from a controller of the monitoring apparatus (indicated as 10), as appropriate, and configured to communicate with the controller.

Other machine readable tagging systems may alternatively, or in addition, be employed. RFID tags are particularly suitable for use with systems embodying the invention as they are inexpensive, can be read at a distance and some types can have data written to them and updated.

The patient contact locations, or target zones, are not limited to beds, and might for example include procedure tables, examination tables, dental chairs, gurneys and/or any location at which a health care worker is likely to come into contact with a patient, or other location where a person is expected to maintain a hygiene standard.

Referring now to FIG. 1B, the system further includes one or more hygiene station monitoring apparatus provided at respective hygiene stations, for example a hand hygiene station (such as an antimicrobial hand rub dispenser 80 (or dispenser of other cleansing substance) and/or hand wash station 21 such a sink with running water and a supply of soap or detergent for hand washing). The hygiene station monitoring apparatus 01 comprises detection apparatus for detecting the approach of a person 03 and/or a tag 05, and wireless communication apparatus for communicating with the tag 05 of a person at the hygiene station. Conveniently, the detection and communication can be performed by an RFID transceiver 24 at the hygiene station apparatus 01 for interacting with the RFID device in the tag 05. Alternatively, or in addition. the hygiene station apparatus 01 may be provided with one or more other sensor, e.g. a PIR detector or other proximity sensor, for detecting the presence of a person at the hygiene station, and other means (e.g. the RFID transceiver 24) for communication between the hygiene station apparatus 01 and the tag 05 once a person has been detected.

Preferably, the RFID transceivers 14, 24, or other suitable component of the monitors 01, 10, are all in communication with a central data processing station 26. Communication could be achieved via a hard-wired connection and/or some other form such as wireless, e.g. radio frequency (RF), communication. In an institution having, for example, a 802.11b or 802.11g or similar type of Wi-Fi based networking or communication system, the RFID transceivers 14, 24 could communicate with the central processing station 26 through such network. A dedicated communication system could alternatively be provided for this purpose. Passive IR personnel detectors 13 can be provided at the hand hygiene stations 01i. Hand hygiene stations 01, especially hand rub dispensers 30 can be mobile and may use magnetic based passive materials.

In its basic operation, the hand hygiene compliance system employs the RFID transceivers 14, 24 along with the personnel tags 05 to help ensure that a person who approaches a patient location has either washed their hands or applied an antimicrobial hand rub to reduce the chance of infecting a patient. This can be implemented in many different fashions. For example, in preferred embodiments, the system supports, in respect of each tag 05, a status indicator that may be set to one of a plurality of states, e.g. "clean" or "potentially contaminated", which indicates a hygiene status assigned to the respective tag 05 by the system. The status indicator, which conveniently takes the form of a data flag, may be maintained by the central processor 26 and/or by the respective tag 05. In one implementation, the hygiene station monitor 01 detects a person's presence at a hand hygiene station 01 and then signals either to the respective tag 05 or to the central processor 26, or to both, that the person's status should be set to "clean". Then when that person subsequently approaches a hospital bed 09 the respective target zone monitor 10 (or more specifically the RFID transceiver 14 associated therewith) reads the RFID device of the tag 05. If the hygiene status is directly encoded within or otherwise stored by the tag 05 (in particular its RFID device), the monitor 10 (or more specifically its RFID transceiver 14) can directly obtain the hygiene status assigned to the tag 05 (and therefore to the person carrying the tag 05) by communicating with the tag 05. Alternatively, where the central processor 26 maintains the status indicator, the monitor 10 may communicate with the central processor 26 to determine the relevant status of the tag 05. To this end, a unique ID may be associated with the tag 05.

Preferably, the monitor 10 incorporates, or is otherwise co-operable with, a visual display 49, and/or an audio output device 50. The display 49 could be as simple as one or more colour-coded lights, preferably labelled, or more complex such an LCD panel. The monitor 10 is advantageously configured to operate the display 49 and/or audio device 50 when it detects the presence of a person in its target zone, and in a manner that depends on the status assigned to the tag 05 carried by that person. For example, when a "clean" person approaches the patient bed 09, the display 49 may indicate the person's status by a green light or display of the status "clean" to show that the person had attended to hand hygiene prior to visiting that hospital bed 09. If the status is not "clean" but i, say, "potentially contaminated", then the monitor 10 generates a warning, e.g. an audio and/or visual warning via the display 49 and/or audio device 50. Preferably, the warning may include a warning light and/or a warning message on the display 49 and an audio alert such as a buzzer or more preferably voice instructions to attend to hand hygiene.

In the preferred embodiment, after a person, who has been detected by the system at a target zone, e.g. bed 09, leaves the target zone, the system is configured to set the respective status to a different value, for example "potentially contaminated". This may be achieved by any suitable method. For example, the monitor 10 may be configured to, upon determining that the respective tag 05 is no longer detected at the target zone or has not been detected at the target zone for more than a threshold period, signal accordingly to the central processor 26 that the respective status should be changed (in cases where the status is maintained by the central processor 26), or signal accordingly to the tag 05 that the respective status should be changed (in cases where the status is maintained by the tag 05). Alternatively, in cases where the status is maintained by the tag 05, the tag 05 may be configured to determine when it has left the target zone and to change its status accordingly. This may be achieved by, for example, the tag 05 determining that it is no longer in contact with the monitor 10, or has not been in contact with the monitor 10 for longer than a threshold period.

In the present example, after leaving the patient bed 09, the RFID device of the tag 05 has the status "potentially contaminated". The status "potentially contaminated" may also be adopted before the tag 05 makes valid contact with any hand hygiene monitor 01, i.e. the "potentially contaminated" state may be an initial, or default, state adopted by the system for tags 05 that have not been detected by a hygiene station monitor 01. The status is changed to "clean" upon determination by a hand hygiene monitor 01 that the tag 05 has made valid contact with the hygiene station monitor 01. The "clean" status may be effective for a specified period of time assuming there is no further contact with patient locations, after which the system may be configured to return the status to the default state, e.g. "potentially contaminated". In more elaborate implementations, sensors such as RFID transceivers may be placed in other locations within a facility which could be possible sources of contamination and contact therewith would change a status from "clean" to "potentially contaminated".

Optionally, the system may be configured to allow a personnel tag 05 to move away from a patient bed 09, or other target zone, and return to that same bed 09 without having the status changed, e.g. from "clean" to "potentially contaminated." This allows, for instance, the person 03 to move about a patient's room without having their status change, or at least the status as respect of that particular patient bed 09. This may be achieved by, for example, not causing a "clean" status of the relevant tag 05 to change to "potentially" "contaminated" until after a period of time has expired since the monitor 10 has detected that the tag 05 has left the zone around the bed 09, which period may be reset if the monitor detects that the same tag re-approaches the bed 09 within said period. Preferably, the "clean" status is time limited so that even if the person 03 re-approaches the bed 09 after that time limit has expired, the status registers as "potentially contaminated." To these ends, the target monitor 10, and/or the central processor 26, may be provided with a timer.

Optionally, compliance rates for personnel can be tracked. The tracking can be performed on the tag 05 itself and/or at the central processor 26. Reports can be generated and used to help personnel improve their compliance. Such reports might include the number of times such personnel approached a patient location with a status other than "clean" within a given time period. could the system may also track which patients were approached and compare tracking data against patient records to track transmission of infections within the institution. Penalties or bonus can be awarded personnel based upon compliance.

If a person 03 approaches a patient bed 09 in a condition other than "clean", the system preferably checks whether such person then proceeds to a hand hygiene station or continues with patient contact. This check may be performed by the target monitor 10 by determining the period of time for which a non-clean tag 05 remains in the target zone, or by the tag 05 itself by determining the period of time for which it remains in the target zone (either or which can for example be achieved by determining the period of time for which the tag 05 and monitor 10 (or more particularly their respective RFID devices) are in contact with one another). To this end, the target monitor 10, and/or the central processor 26, may be provided with a timer and/or a clock. An exception in this area may be flagged with a higher priority by the system. The check may also, or alternatively, be made by comparing time at which the tag 05 is present at the bed 09 with the time of the tag's next appearance at a hand hygiene station, and possibly whether such personnel then return to the same bed 09. For instance, spending more than five or ten seconds, or other threshold period, at the bed 09 in a state other than "clean" might constitute a violation.

Compliance at a hand hygiene station can either be assumed by presence (i.e. a valid detection of a tag 05 by a monitor 01 is taken to indicate that the person 03 has performed the relevant hygiene activity), or assumed by presence of the tag 05 for a given amount of time, and/or verified by one or more sensors at the hand hygiene station, or included in the monitor 01, e.g. a sensor that detects when soap is dispensed at a hand wash station, and/or a sensor that detects when an antimicrobial hand gel, or other substance, has been dispensed at a hand rub dispenser 80. Such sensors are particularly advantageous when the hand hygiene station comprises a portable dispenser 80 worn on the body of the user. In such cases, the respective hygiene station monitor does not need to detect the presence of the tag 05 since the tag 05 is also carried by the person. Accordingly, the hygiene station monitor may be configured to set the status of the tag's status indicator to "clean" upon determining, e.g. by means of an appropriate sensor provided on the mobile dispenser, that the dispenser has been operated. Advantageously, the hygiene station monitor still includes means for detecting the presence of the tag 05 so that, in an initial operation, it can detect the tag 05 and thereafter update the tag's status indicator depending on operation of the dispenser rather than by detection of the tag until it detects that the tag 05 is removed from its vicinity, e.g. when the user takes the dispenser off. Alternatively, the hygiene station monitor may broadcast a signal for updating status indicators when it determines that the dispenser has been operated, which signal may be received by any tag 05 that is close enough to the hygiene station monitor.

Hand hygiene procedures typically require a certain length of scrubbing at hand wash stations 21 and the time of water running after dispensing of the soap might also be measured for the purpose of determining compliance. A proximity sensor, especially one already used to turn on water flow, might also be polled to see if hands are in the stream of the water. Many faucets already incorporate such sensors.

Optionally, the personnel tags 05 may include audio and/or visual displays. For instance, the tag 05 might bear one or more lamps, e.g. a lamp such as an LED that is operable in more than one colour, or separate lamps 91, 92 (FIG. 2) for each status, and optionally a beeper 93, or other audio device, which emits a tone upon a change in status, or when a status other than clean is registered. Preferably, the tags 05 are provided with powered, or active, RFID devices which have improved communication ranges over passive RFID tags, and a common power source could power all of the features of such tags 05.

In alternative embodiments, the hygiene compliance system may employ multiple detectors/monitors 10 throughout a facility, e.g. a building, which are configured to read and locate personnel tags 05 and specific events. In such a system, a person's exact location within a facility may be tracked and sensors may be activated to record specific events, such as opening a fridge, removing food and/or opening a drugs cabinet.

Optionally, the tag 05 can be embedded in a uniform, or other clothing. Temperature and wash cycles could similarly be monitored, incorporated e.g. by means of a temperature sensor located in, for example, clothing or textiles.

In preferred systems a tag 05' is incorporated into a respective washable item, especially an item of clothing, the tag being associated with a respective status indicator that is settable to a first value indicating hygiene compliance, e.g. denoting that the item is washed, or to a second value indicating hygiene non-compliance, e.g. denoting that the item needs washed. The tag further includes a temperature sensor that, in response to detecting a temperature above a threshold temperature, e.g. during a wash cycle in a washing machine, is configured to cause its status indicator to be set to the first value. The tag 05' may be similar to the tag 05 described above and so similar descriptions apply as would be apparent to the skilled person. For example, the tag 05' may comprise an RFID device, especially an RFID transponder, for communicating with, and preferably also for detection by, other components of the system, e.g. the monitors 01, 10. Alternatively, the tag 05' may comprise any other suitable means, e.g. wireless transceiver, to allow it to communicate with a preferably to be detected by, other components of the system.

Preferably, the tag '05 includes an alarm device, preferably an audio alarm device, the tag including means for activating the audio alarm device in response to determining that the respective status indicator is set to the second value. Optionally, the tag '05 maintains its own respective status indicator, e.g. in a local memory device or register. Alternatively, the respective status indicator is maintained by a central processor, conveniently processor 26.

The tag 05' may comprise a counter with which can count the number of times it is washed, i.e. by counting the number of times its status indicator is set to the first value.

Preferably, the status indicator is set to the second value after a period of time has elapsed after having been set to the first value. Optionally, said respective status indicator is set to said second value depending on the date and/or time. To these ends, each tag may include a timer and/or a clock, especially a clock that supports a calendar.

The embedded tags are particularly suitable for use with machine washable articles such as clothing, bed linen, and towels. By way of example, the temperature threshold may be approximately 70° C.

In preferred embodiments, the tags 05' communicate with other systems components, conveniently the monitors 01, 10, to transfer data concerning the laundry history of the respective item in which it is embedded, e.g. the value of the respective status indicator, the value of the counter and/or one or more date(s) and/or time(s) at which the item has been washed. This allows the data to be sent to a central processor for evaluation and/or recordal.

It will be understood that, while the tag '05 is particularly suited for use with the system of FIGS. 1A to 1C, it may alternatively be used in other systems, with or without the tag 05.

The invention is not limited to the embodiments described herein, which may be modified or varied without departing from the scope of the invention.

The invention claimed is:

1. A hygiene compliance system comprising:
at least one personnel tag for carrying by a respective person, said at least one personnel tag being associated with a respective status indicator that is settable to a first value indicating hygiene compliance or to a second value indicating hygiene non-compliance,
at least one target zone monitoring apparatus for monitoring a respective target zone, said at least one target zone monitoring apparatus including at least one sensor for detecting said at least one personnel tag at the respective target zone,
at least one hygiene station monitoring apparatus for monitoring a respective hygiene station, and
wherein a respective hygiene compliance record is stored for said at least one personnel tag,
and wherein, upon determining that the respective hygiene station has been used, said at least one hygiene station monitoring apparatus is configured to cause the respective status indicator of the at least one personnel tag to be set to said first value,
and wherein, upon detecting any one of said at least one personnel tag at said respective target zone, said target zone monitoring apparatus is configured to determine a value of the respective status indicator without changing the value of the respective status indicator, and to cause the determined value to be recorded in the respective hygiene compliance record for detected personnel tag,
and wherein, upon determining that any one of the at least one personnel tag has left the respective target zone, the system is configured to cause the respective status indicator to be set to said second value.

2. The system as claimed in claim 1, wherein, upon determining that any one of said at least one personnel tags has left the respective target zone, the respective target zone monitoring apparatus is configured to cause the respective status indicator to be set to said second value.

3. The system as claimed in claim 1, wherein said system is configured to cause the respective status indicator of said at least one personnel tag to be set to said second value when a pre-determined time period has elapsed after said respective status indicator has been set to said first value.

4. The system as claimed in claim 3, wherein said at least one personnel tag is configured to cause the respective status indicator to be set to said second value when a pre-determined time period has elapsed after said respective status indicator has been set to said first value.

5. The system as claimed in claim 1, configured to delay changing a value of said status indicator from said first value to said second value for a period of time after determining that the at least one personnel tag has left the target zone and, upon detecting that said personnel tag re-enters a target zone within said period of time, to maintain said respective status indicator at said first value.

6. The system as claimed in claim 1, wherein said at least one hygiene station monitoring apparatus including at least one sensor for detecting said at least one personnel tag at the respective hygiene station.

7. The system as claimed in claim 6, wherein, upon detection of any one of said at least one personnel tag at the respective hygiene station, said at least one hygiene station monitoring apparatus is configured to cause the respective status indicator of the detected personnel tag to be set to said first value.

8. The system as claimed in claim 6, wherein said at least one hygiene station monitoring apparatus comprises at least one sensor for detecting operation of the respective hygiene station, and wherein, upon detecting the operation of the respective hygiene station, said at least one hygiene station monitoring apparatus is configured to cause the respective status indicator of a detected personnel tag or other associated personnel tag to be set to said first value.

9. The system as claimed in claim 8, wherein said at least one hygiene station monitoring apparatus and respective hygiene station are provided as a portable dispenser, suitable for carrying by a person.

10. The system as claimed in claim 1, wherein said at least one target zone monitoring apparatus includes a visual display device for indicating a value of the respective status indicator of a detected personnel tag.

11. The system as claimed in claim 1, wherein said at least one target zone monitoring apparatus includes an audio output device for indicating the value of the respective status indicator of a detected personnel tag.

12. The system as claimed in claim 1, wherein said at least one target zone monitoring apparatus includes an alarm device for generating an alarm when the respective status indicator of a detected personnel tag is set to said second value.

13. The system as claimed in claim 1, wherein said at least one target zone monitoring apparatus and said at least one personnel tag each comprises a wireless communication device for communicating with one another.

14. The system as claimed in claim 1, wherein said at least one hygiene station monitoring apparatus and said at least one personnel tag each comprises a wireless communication device for communicating with one another.

15. The system as claimed in claim 1, wherein said at least one sensor for detecting said at least one personnel tag at the respective target zone is configured to indirectly detect said at least one personnel tag by being configured to detect a presence of a person in said respective target zone.

16. The system as claimed in claim 15, wherein presence detector is arranged to define a detection perimeter around said target zone and to detect a person crossing said perimeter.

17. The system as claimed in claim 15, wherein presence detector comprises at least one of a proximity sensor, a motion sensor, and a through-beam sensor.

18. The system as claimed in claim 1, wherein said at least one sensor for detecting said at least one personnel tag at the respective hygiene station is configured to indirectly detect said at least one personnel tag by being configured to detect a presence of a person at said respective hygiene station.

19. The system as claimed in claim 18, wherein presence detector comprises at least one of a proximity sensor, a motion sensor, and a through-beam sensor.

20. The system as claimed in claim 1, wherein said at least one target zone monitoring apparatus comprises wireless transceiver, which is an RFID device, for communicating with said at least one personnel tag and detecting said at least one personnel tag.

21. The system as claimed in claim 1, wherein said at least one hygiene station monitoring apparatus comprises wireless transceiver, which is an RFID device, for communicating with said at least one personnel tag and detecting said at least one personnel tag.

22. The system as claimed in claim 1, wherein said at least one personnel tag comprises a wireless transceiver, preferably an RFID transponder.

23. The system as claimed in claim 1, further comprising a central processor in communication with at least said at least one target monitoring zone and preferably arranged to maintain said status indicators.

24. A method of monitoring hygiene compliance in a system comprising:
  at least one personnel tag for carrying by a respective person, said at least one personnel tag being associated with a respective status indicator that is settable to a first value indicating hygiene compliance or to a second value indicating hygiene non-compliance,
  at least one target zone monitoring apparatus for monitoring a respective target zone, said at least one target zone monitoring apparatus including at least one sensor for detecting said at least one personnel tag at the respective target zone,
  at least one hygiene station monitoring apparatus for monitoring a respective hygiene station, and
  said method comprising storing a respective hygiene compliance record for said at least one personnel tag,
  upon determining that a hygiene station has been used, causing the respective status indicator of the at least one personnel tag to be set to said first value, and
  upon detecting any one of said at least one personnel tag at said respective target zone, determining a value of the respective status indicator without changing the value of the respective status indicator, and to cause the determined value to be recorded in the respective hygiene compliance record for the detected personnel tag, and
  upon determining that any one of said at least one personnel tag has left the respective target zone, causing the respective status indictor to be set to said second value.

25. The system as claimed in claim 1, comprising at least one tag incorporated into a respective washable item said at least one tag being associated with a respective status indicator that is settable to the first value indicating hygiene compliance or to the second value indicating hygiene non-compliance, said at least one tag further including a temperature sensor that, in response to detecting a temperature above a threshold temperature, is configured to cause said status indicator to be set to said first value.

26. The system as claimed in claim 25, wherein said at least one tag includes an alarm device, preferably an audio alarm device, said at least one tag including being configured to activate said audio alarm device in response to determining that the respective status indicator is set to said second value.

27. The system as claimed in claim 25, wherein said system is configured to set said respective status indicator to said second value after a period of time has elapsed after having been set to said first value.

28. A hygiene compliance system comprising
  at least one personnel tag for carrying by a respective person, said at least one personnel tag being associated with a respective status indicator that is settable to a first value indicating hygiene compliance or to a second value indicating hygiene non-compliance,
  at least one target zone monitoring apparatus for monitoring a respective target zone, said at least one target zone monitoring apparatus including at least one sensor for detecting said at least one personnel tag at the respective target zone,
  at least one hygiene station monitoring apparatus for monitoring a respective hygiene station, and
  wherein, upon determining that the respective hygiene station has been used, said at least one hygiene station monitoring apparatus is configured to cause the respective status indicator of the at least one personnel tag to be set to said first value,
  and wherein, upon detecting any one of said at least one personnel tag at said respective target zone, said target zone monitoring apparatus is configured to determine a value of the respective status indicator,
  and wherein, upon determining that any one of the at least one personnel tag has left the respective target zone, the system is configured to cause the respective status indicator to be set to said second value,
  and wherein the system is configured to delay changing detected value of said status indicator from said first value to said second value for a period of time after determining that respective personnel tag has left the target zone and, upon detecting that said respective personnel tag re-enters a target zone within said period of time, to maintain said respective status indicator at said first value.

* * * * *